(12) United States Patent
Colacot et al.

(10) Patent No.: US 8,772,520 B2
(45) Date of Patent: Jul. 8, 2014

(54) PREPARATION OF A METAL COMPLEX

(75) Inventors: Thomas John Colacot, Cherry Hill, NJ (US); Gabriela Alexandra Grasa, Bowie, MD (US); Hongbo Li, Thorofare, NJ (US)

(73) Assignee: Johnson Matthey Public Limited Company, London (GB)

(*) Notice: Subject to any disclaimer, the term of this patent is extended or adjusted under 35 U.S.C. 154(b) by 183 days.

(21) Appl. No.: 13/318,970

(22) PCT Filed: Jan. 12, 2010

(86) PCT No.: PCT/GB2010/050035
§ 371 (c)(1),
(2), (4) Date: Jan. 23, 2012

(87) PCT Pub. No.: WO2010/128316
PCT Pub. Date: Nov. 11, 2010

(65) Prior Publication Data
US 2012/0116109 A1      May 10, 2012

Related U.S. Application Data

(60) Provisional application No. 61/175,942, filed on May 6, 2009.

(51) Int. Cl.
C07F 15/00   (2006.01)
C07F 9/02    (2006.01)

(52) U.S. Cl.
USPC ............................................ 556/23; 556/104

(58) Field of Classification Search
USPC .................................................. 556/23, 104
See application file for complete search history.

(56) References Cited

U.S. PATENT DOCUMENTS

| 4,196,135 A | 4/1980 | Enomoto et al. |
| 5,919,981 A | 7/1999 | Chan et al. |
| 6,720,281 B2 | 4/2004 | Leitner et al. |
| 6,906,212 B1 | 6/2005 | Boaz |

FOREIGN PATENT DOCUMENTS

| JP | 63264594 A | 11/1988 |
| WO | WO-02/26750 A2 | 4/2002 |
| WO | WO-2004/111065 A1 | 12/2004 |
| WO | WO-2008/041029 A1 | 4/2008 |

OTHER PUBLICATIONS

Grasa et al., "α-Arylation of Ketones Using Highly Active, Air-Stable (DtBPF)PdX$_2$ (X=Cl, Br) Catalysts," *Organic Letters* 2007, vol. 9, No. 26, pp. 5489-5492.

(Continued)

*Primary Examiner* — Porfirio Nazario Gonzalez
(74) *Attorney, Agent, or Firm* — Young & Thompson

(57) ABSTRACT

The present invention provides a process for the preparation of a Pd(0)L$_n$ complex, where L is a ligand and n is 2, 3 or 4, comprising the steps of: (a) reacting a Pd(II) complex in at least one solvent with a base and ligand L; and (b) if required, adding further base, optionally in at least one solvent, to form the Pd(0)L$_n$ complex; wherein the at least one solvents in steps a and b are independently the same or different, and provided that when n=2, the Pd(II) complex is not bis[tri(ortho-tolyl)phosphine] palladium chloride. The invention also provides novel Pd(0)L$_2$ and Pd(II) complexes.

29 Claims, 1 Drawing Sheet

(56) References Cited

OTHER PUBLICATIONS

Yoshida et al., "Two-Coordinate Phosphine Complexes of Palladium(0) and Platinum(0)," in Inorganic Syntheses: Reagents for Transition Metal Complex and Organometallic Syntheses, vol. 28, ed. R. J. Angelici (John Wiley & Sons, Inc., 2007), pp. 113-119.

Norton et al., "A Superior Precursor for Palladium(0)-Based Cross-Coupling and Other Catalytic Reactions," *J. Org. Chem.* 2009, vol. 74, No. 17, pp. 6674-6680.

Paul et al., "Structural Characterization and Simple Synthesis of {Pd[P(o-Tol)$_3$]$_2$}, Dimeric Palladium(II) Complexes Obtained by Oxidative Addition of Aryl Bromides, and Corresponding Monometallic Amine Complexes," *Organometallics* 1995, vol. 14, pp. 3030-3039.

Tang et al., "New Chiral Phosphorus Ligands for Enantioselective Hydrogenation," *Chem. Rev.* 2003, vol. 103, pp. 3029-3069.

Carretero et al., "Recent Applications of Chiral Ferrocene Ligands in Asymmetric Catalysis," *Angew. Chem. Int. Ed.* 2006, vol. 45, pp. 7674-7715.

Mann et al., "Electronic and Steric Effects on the Reductive Elimination of Diaryl Ethers from Palladium(II)," *Organometallics* 2003, vol. 22, pp. 2775-2789.

Hills et al., "Elucidating Reactivity Differences in Palladium-Catalyzed Coupling Processes: The Chemistry of Palladium Hydrides," *J. Am. Chem. Soc.* 2004, vol. 126, pp. 13178-13179.

Hill et al., "Neopentylphosphines as effective ligands in palladium-catalyzed cross-couplings of aryl bromides and chlorides," *Tetrahedron* 2008, vol. 64, pp. 6920-6934.

International Search Report dated Mar. 22, 2010, from PCT International Application No. PCT/GB2010/050035.

Otsuka et al., "Bis(tertiary phosphine)palladium(0) and -platinum(0) Complexes: Preparations and Crystal and Molecular Structures", Journal of the American Chemical Society, 1976, vol. 98, No. 19, pp. 5850-5858.

PREPARATION OF A METAL COMPLEX

CROSS-REFERENCE TO RELATED APPLICATIONS

This application is the U.S. National Phase application of PCT International Application No. PCT/GB2010/050035, filed Jan. 12, 2010, and claims priority of U.S. Provisional Patent Application No. 61/175,942, filed May 6, 2009, the disclosures of both of which are incorporated herein by reference in their entireties for all purposes.

FIELD OF THE INVENTION

The present invention concerns the preparation of metal complexes, in particular, Pd(0) complexes.

BACKGROUND OF THE INVENTION

Over the past two decades, palladium-catalyzed cross coupling technology has emerged as one of the most powerful tools in organic synthesis, both in academia and industry. Although either Pd(II) or Pd(0) in conjunction with a ligand can facilitate the cross coupling catalysis, it is well established that $L_nPd(0)$ ($L_n$=number of ligands) is the active catalytic species in the cycle. However during the initial step of reducing Pd(II) to Pd(0), there seems to be a lack of careful studies to understand the mechanism.

There is an increasing interest in using pre-formed Pd(0) $(R_3P)_2$ complexes as catalysts, instead of generating the catalyst in situ, as it avoids handling pyrophoric or air sensitive phosphine ligands, eliminates induction periods, and reduces undesired side products or sometimes no reaction (Grasa, G. A.; Colacot, T. J *Org. Lett.* 2007, 9, 5489). However, there are not many examples of $Pd(0)(R_3P)_2$ catalysts available commercially today, as their synthesis and scale up are tedious. A few methods are reported in the literature for the synthesis of $Pd(0)(R_3P)_2$ compounds. The method using $Pd(\eta^3-C_3H_5)(\eta^5-C_5H_5)$ as a precursor (Yoshida, T.; Otsuka, S. *Inorg. Synth.* 1990, 28, 113) often suffers from its instability and volatility (Norton, D. M.; Mitchell, E. A.; Botros, N. R.; Jessop, P. G.; Baird, M. C. *J. Org. Chem.*, 2009, 74, 6674); while the route involving $Pd_2(dba)_3$ (Hartwig, J. F. *Organometallics* 1995, 14, 3030) often requires recrystallization, which uses large amount of solvent under cryogenic conditions, therefore difficult to scale-up. More recently, $Pd(\eta^3-1-PhC_3H_4)(\eta^5-C_5H_5)$ is reported (Norton, D. M.; Mitchell, E. A.; Botros, N. R.; Jessop, P. G.; Baird, M. C. *J. Org. Chem.*, 2009, 74, 6674) to be a new precursor to synthesize $L_2Pd(0)$ in situ, although its scalability for industrial production is still unknown.

U.S. Pat. No. 4,196,135 describes the preparation of $Pd[(o-tol)_3]_2$. However, this method could not be reproduced. The major by-product was a black insoluble material, typical of reduced palladium and the starting palladium(II) complex. Hartwig et al. were also not able to reproduce this synthesis even by changing the reaction conditions (Hartwig, J. F. *Organometallics* 1995, 14, 3030).

SUMMARY OF THE INVENTION

It is an object of the present invention to provide an alternative process for the preparation of Pd(0) metal complexes. The process is general, safe and efficient and may be carried out on an industrial scale. Moreover, the process may use readily available, inexpensive, air-stable precursors and in some embodiments nearly quantitative yields of the complexes may be obtained.

In one aspect, the invention provides a process for the preparation of a $Pd(0)L_n$ complex, where L is a ligand and n is 2, 3 or 4, comprising the steps of:
   a. reacting a Pd(II) complex in at least one solvent with a base and a ligand L; and
   b. if required, adding further base, optionally in at least one solvent, to form the $Pd(0)L_n$ complex;
wherein the at least one solvents in steps a and b are independently the same or different, and
provided that when n=2, the Pd(II) complex is not bis[tri(ortho-tolyl)phosphine] palladium chloride.

In another aspect, the invention provides a process for the preparation of a Pd(II) complex of formula 2a or 2b:

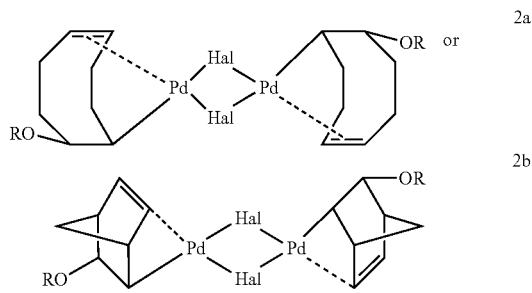

comprising the step of reacting Pd(diolefin)(Hal)$_2$ with (i) hydroxide in water, (ii) an alkoxide in solvent, or (iii) hydroxide in an alcohol ROH, optionally in at least one solvent,
wherein,
each Hal is independently a halide;
each R is independently H or an optionally substituted $C_{1-15}$ straight-chain, branched or cyclic alkyl group; and
the diolefin is cyclooctadiene or norbornadiene.

In yet another aspect, the invention provides a process for the preparation of a $L_2Pd(H)(Hal)$ complex comprising the steps of:
   a'. optionally preparing a Pd(II) complex of formula 2a or 2b:

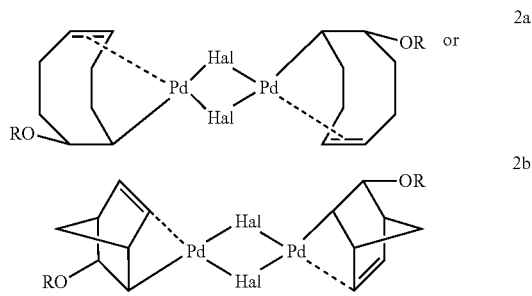

comprising reacting Pd(diolefin)(Hal)$_2$ with a base in (i) hydroxide in water, (ii) an alkoxide in solvent, or (iii) hydroxide in an alcohol ROH, optionally in at least one solvent,
   wherein,
   each Hal is independently a halide;
   each R is independently H or an optionally substituted C1-15 straight-chain, branched or cyclic alkyl group; and the diolefin is cyclooctadiene or norbornadiene; and b'. reacting the Pd(II) complex of formula 2a or 2b with ligand L and, if required, at least one solvent, to form the $L_2Pd(H)(Hal)$ complex;

wherein, the at least one solvents of steps a' and b' are independently the same or different.

In another aspect, the invention provides a Pd(II) complex of formula 2a or 2b:

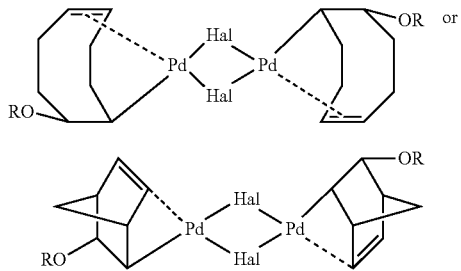

wherein each Hal is independently a halide, and each R is independently H or an optionally substituted $C_{1-15}$ straight-chain, branched or cyclic alkyl group.

In yet another aspect, the invention provides a $Pd(0)L_2$ complex which is $[t-Bu_2(p-PhMe_2N)P]_2Pd$.

In another aspect, the invention provides Pd[di-tert-butyl-neopentylphosphine]$_2$ obtainable by the process as defined herein.

DETAILED DESCRIPTION OF CERTAIN EMBODIMENTS OF THE INVENTION

Figure 1:
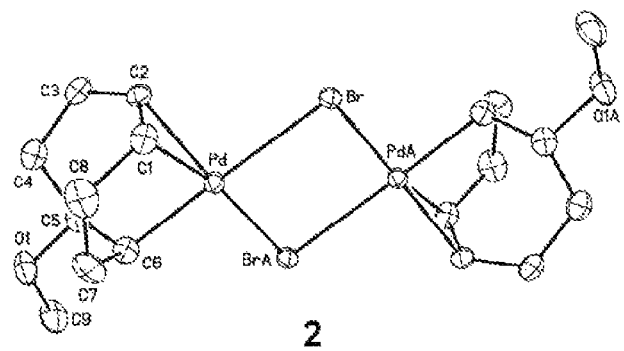
FIG. 1 is the X-ray crystallographic structure of di-μ-bromo[(1,4,5-η)-8-methoxy-4-cycloocten-1-yl]dipalladium, 9Br.

As mentioned, one aspect of the present invention is to provide a process for the preparation of a $Pd(0)L_n$ complex, where L is a ligand and n is 2, 3 or 4, comprising the steps of:

a. reacting a Pd(II) complex in at least one solvent with a base and a ligand L; and b. if required, adding further base, optionally in at least one solvent, to form the $Pd(0)L_n$ complex;

wherein the at least one solvents in steps a and b are independently the same or different, and provided that when n=2, the Pd(II) complex is not bis[tri(ortho-tolyl)phosphine] palladium chloride.

In one embodiment, n is 2 or 4. The $Pd(0)L_n$ complexes therefore are $Pd(0)L_2$ and $Pd(0)L_4$.

In one embodiment, the Pd(II) complex is selected from the group consisting of $Pd(olefin)_x(Hal)_2$, $Pd(Hal)_2$, $Pd(phosphine)_y(Hal)_2$ and $M_2Pd(Hal)_4$, wherein, each Hal is independently a halide, M is a cation, x and y are independently 1 or 2, and wherein, when x=1, the olefin is a diolefin, when x=2, the olefin is a mono-olefin, when y=1, the phosphine is a bidentate phosphine, and when y=2, the phosphine is a monophosphine.

When n=2, the Pd(II) complex is preferably $Pd(olefin)_x(Hal)_2$, $Pd(Hal)_2$ or $M_2Pd(Hal)_4$, especially $Pd(olefin)_x(Hal)_2$.

Preferably, the diolefin contains a cyclic diolefin, more preferably 2,5-norbornadiene (NBD) or 1,5-cyclooctadiene (COD). Alternatively the cyclic diolefin can be replaced by either two molecules of an olefin such as ethylene or two molecules of a $C_{5-10}$ cycloalkene.

The halide may be chloride, bromide or iodide, preferably chloride or bromide. As used herein, "halide" and "Hal" may be used interchangeably.

The cation M may be an alkali metal cation (e.g. $Na^+$ or $K^+$) or an ammonium ion cation ($NH_4^+$).

The $M_2Pd(Hal)_4$ complex may be prepared in situ by reacting a $Pd(Hal)_2$ complex with an alkali metal salt or ammonium salt. Preferably, the salt is an alkali metal halide (such as NaCl, NaBr, KCl or KBr) or ammonium halide salt (such as $NH_4Cl$ or $NH_4Br$). Examples of $M_2Pd(Hal)_4$ complexes formed therefore are $Na_2Pd(Hal)_4$, $K_2Pd(Hal)_4$ and $(NH_4)_2Pd(Hal)_4$. The advantage of preparing a $M_2Pd(Hal)_4$ complex in situ is that a complex of this type is usually more soluble and more reactive than $Pd(Hal)_2$.

Suitable Pd(II) complexes include $PdCl_2$ (e.g. $PdCl_2$ salt or $PdCl_2$ aqueous solution), $PdBr_2$, $Pd(diolefin)(halide)_2$ complexes such as $Pd(COD)Br_2$, $Pd(COD)Cl_2$, $Pd(NBD)Br_2$, $Pd(NBD)Cl_2$, $Pd(monophosphine)_2(Hal)_2$ complexes such as $Pd(PPh_3)_2Cl_2$ and $M_2Pd(Hal)_4$ complexes such as $Na_2PdCl_4$, $K_2PdCl_4$ or $(NH_4)_2PdCl_4$.

The Pd(II) complex is present in at least one solvent and may be in the form of a suspension or solution. The solvent used may be any suitable solvent and may be selected from protic solvents, aprotic solvents or combinations thereof. Examples of protic solvents are water or alcohols (such as methanol, ethanol, 1-propanol, 2-propanol, 1-butanol, 2-butanol, t-butanol or benzylic alcohol). Examples of aprotic solvents are aromatic solvents (such as toluene or benzene), ethers (e.g. tetrahydrofuran (THF), dioxane, methyltertbutylether (MTBE) or diethylether), ketones (such as acetone), esters (e.g. ethylacetate), nitriles (such as acetonitrile), amides (e.g. dimethylformamide (DMF), N-methylpyrrolidine (NMP) or dimethylacetamide (DMAc)) or alkanes (such as isomers of pentane, hexane or heptane). Particularly preferred solvents are water, alcohols and/or aromatic solvents, especially water, methanol, ethanol and/or toluene.

The base may be a hydroxide, alkoxide, carbonate, acetate or phosphate and preferably, hydroxide or alkoxide.

Suitable hydroxides include alkali metal hydroxides (e.g. lithium hydroxide, sodium hydroxide or potassium hydroxide) or tetraalkylammonium hydroxides. Preferred hydroxides are sodium hydroxide, potassium hydroxide or tetrabutylammonium hydroxide.

Suitable alkoxides include alkali metal alkoxides (e.g. lithium alkoxide, sodium alkoxide or potassium alkoxide) or tetraalkylammonium alkoxides. A preferred alkoxide is sodium methoxide.

As used herein, the term "alkyl" refers to an optionally substituted cyclic, branched or straight chain saturated hydrocarbon group preferably having 1 to 15 carbon atoms, more preferably 1 to 10 carbon atoms, most preferably 1 to 5 carbon atoms. Examples of $C_1$-$C_{15}$ alkyl groups include, but are not limited to, methyl, ethyl, n-propyl, isopropyl, n-butyl, t-butyl, n-pentyl, cyclopentyl, n-hexyl, cyclohexyl and the like. The term "alkoxide" should be construed accordingly.

Suitable carbonates include alkali metal carbonates (e.g. lithium carbonate, sodium carbonate or potassium carbonate). A preferred carbonate is sodium carbonate.

Suitable phosphates include alkali metal phosphates (e.g. lithium phosphates, sodium phosphates or potassium phosphates). A preferred phosphate is sodium phosphate.

Suitable acetates include alkali metal acetates (e.g. lithium acetates, sodium acetates or potassium acetates). A preferred acetate is sodium acetate.

The base is preferably present in stoichiometric quantities or excess to the Pd(II) complex.

The base may be added to the reaction mixture as a solution in at least one solvent. Suitable solvents will generally be similar to those previously mentioned in connection with the Pd(II) complex. When the solvent is a protic solvent, the solvent may be water, an alcohol or a combination thereof. Methanol and/or water are particularly preferred. In one embodiment, the at least one solvent comprises a protic solvent when the base is a hydroxide, carbonate, phosphate or acetate.

When the solvent is aprotic, aromatic solvents are preferred, in particular, toluene. In one embodiment, the solvent is an aprotic solvent when the base is an alkoxide.

When the Pd(II) complex is Pd(diolefin)(halide)$_2$, it has been discovered that a Pd(II) dimer is formed as an intermediate on reaction of the Pd(diolefin)(halide)$_2$ with a base in a solvent. It is possible to isolate the Pd(II) dimer using methods known to a person skilled in the art before reacting the complex with the ligand L (if desired). Alternatively, it is also possible to add a solution of the ligand L directly to the solution of the Pd(II) dimer.

When the base is a hydroxide in water, the inventors believe the Pd(II) dimer formed is a Pd(II) (hydroxyl-olefin)dimer. When the base is an alkoxide or hydroxide in alcohol, the inventors believe the Pd(II) dimer formed is a Pd(II) (alkoxy-olefin)dimer.

The ligand L may be a phosphorus compound. Any suitable phosphorus compound capable of forming a ligand-metal interaction with the Pd atom may be used. In the ligand, each phosphorus atom is covalently bonded to either 3 carbon atoms (tertiary phosphines) or to z heteroatoms and 3-z carbon atoms, where z=1, 2 or 3. Preferably, the heteroatom is selected from the group consisting of N and O.

The phosphorus ligand may be monodentate, e.g. PPh$_3$, or bidentate. The ligand may be chiral or achiral, although in many instances it is preferred that the phosphorus ligand is chiral. A variety of chiral phosphorus ligands has been described and reviews are available, for example see W. Tang and X. Zhang, Chem Rev. 2003, 103, 3029-3070 and J. C. Carretero, Angew. Chem. Int. Ed., 2006, 45, 7674-7715. Phosphorus ligands that may be used in the present invention include but are not restricted to the following structural types:

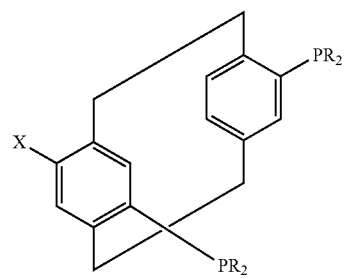

PARAPHOS
X = functional group
R = aryl, akyl including X = H:

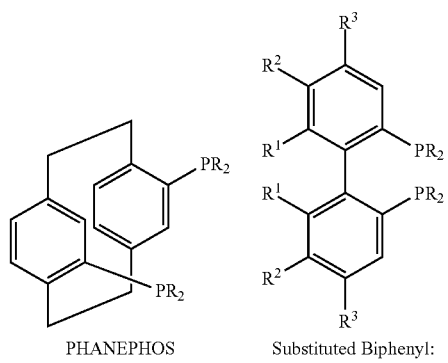

PHANEPHOS

Substituted Biphenyl:
R = aryl and akyl
R$^1$ = alkyl, alkoxy
R$^2$ = H, alkyl, alkoxy, halide
R$^3$ = H, alkyl including:

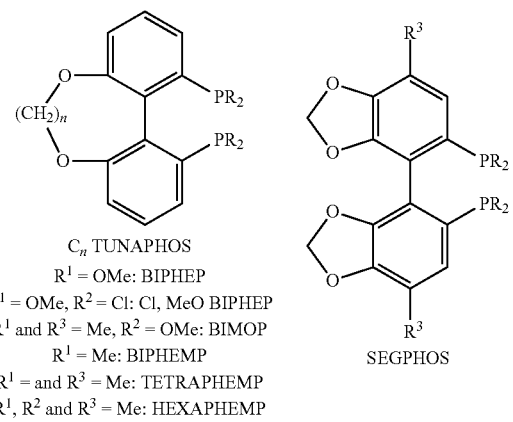

C$_n$ TUNAPHOS
R$^1$ = OMe: BIPHEP
R$^1$ = OMe, R$^2$ = Cl: Cl, MeO BIPHEP
R$^1$ and R$^3$ = Me, R$^2$ = OMe: BIMOP
R$^1$ = Me: BIPHEMP
R$^1$ = and R$^3$ = Me: TETRAPHEMP
R$^1$, R$^2$ and R$^3$ = Me: HEXAPHEMP

SEGPHOS

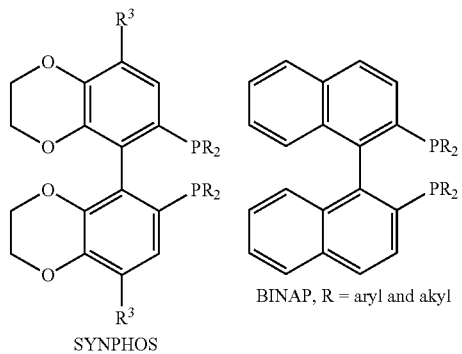

SYNPHOS

BINAP, R = aryl and akyl

-continued
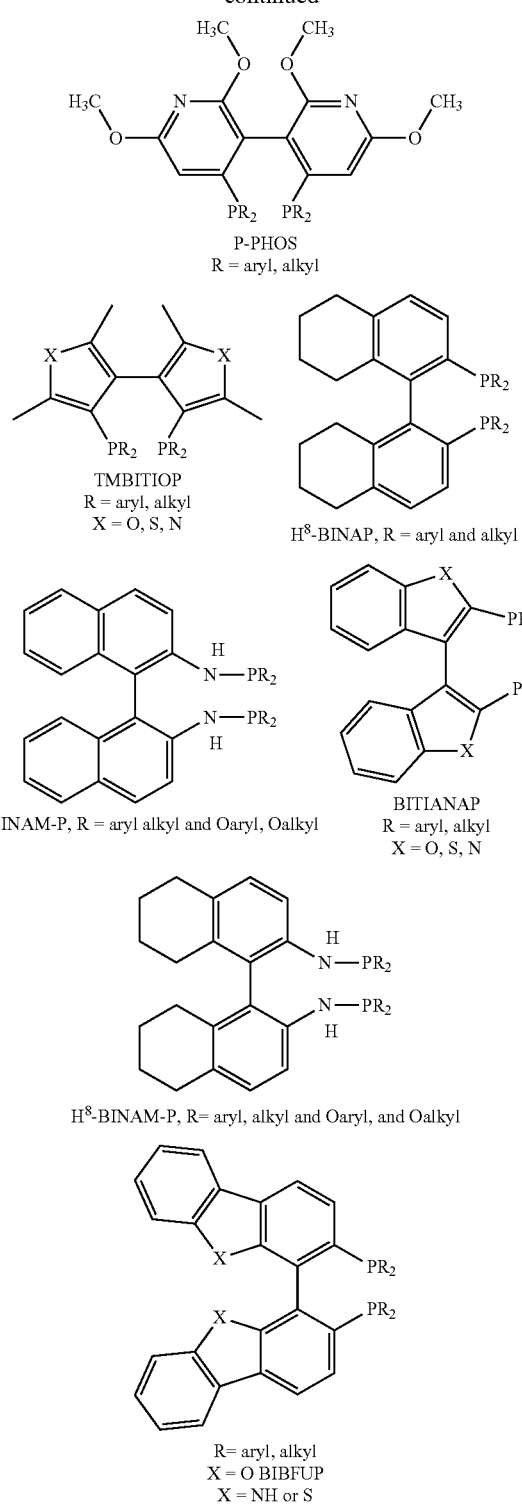
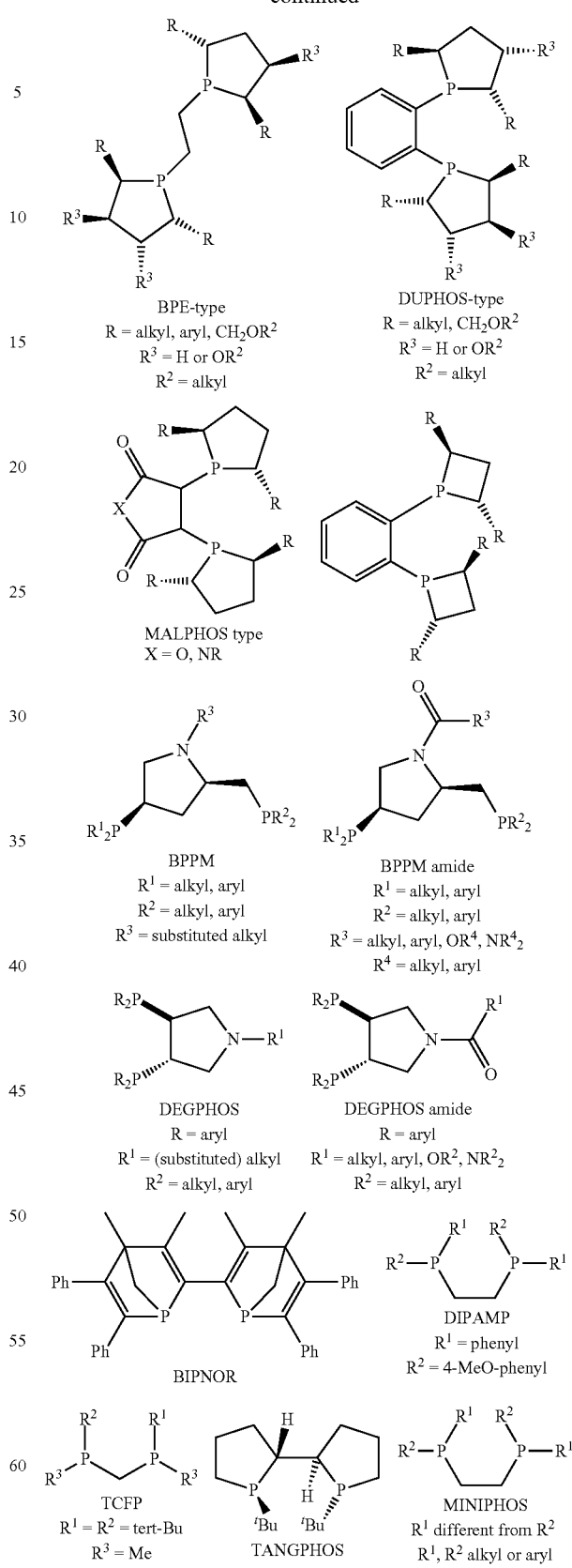

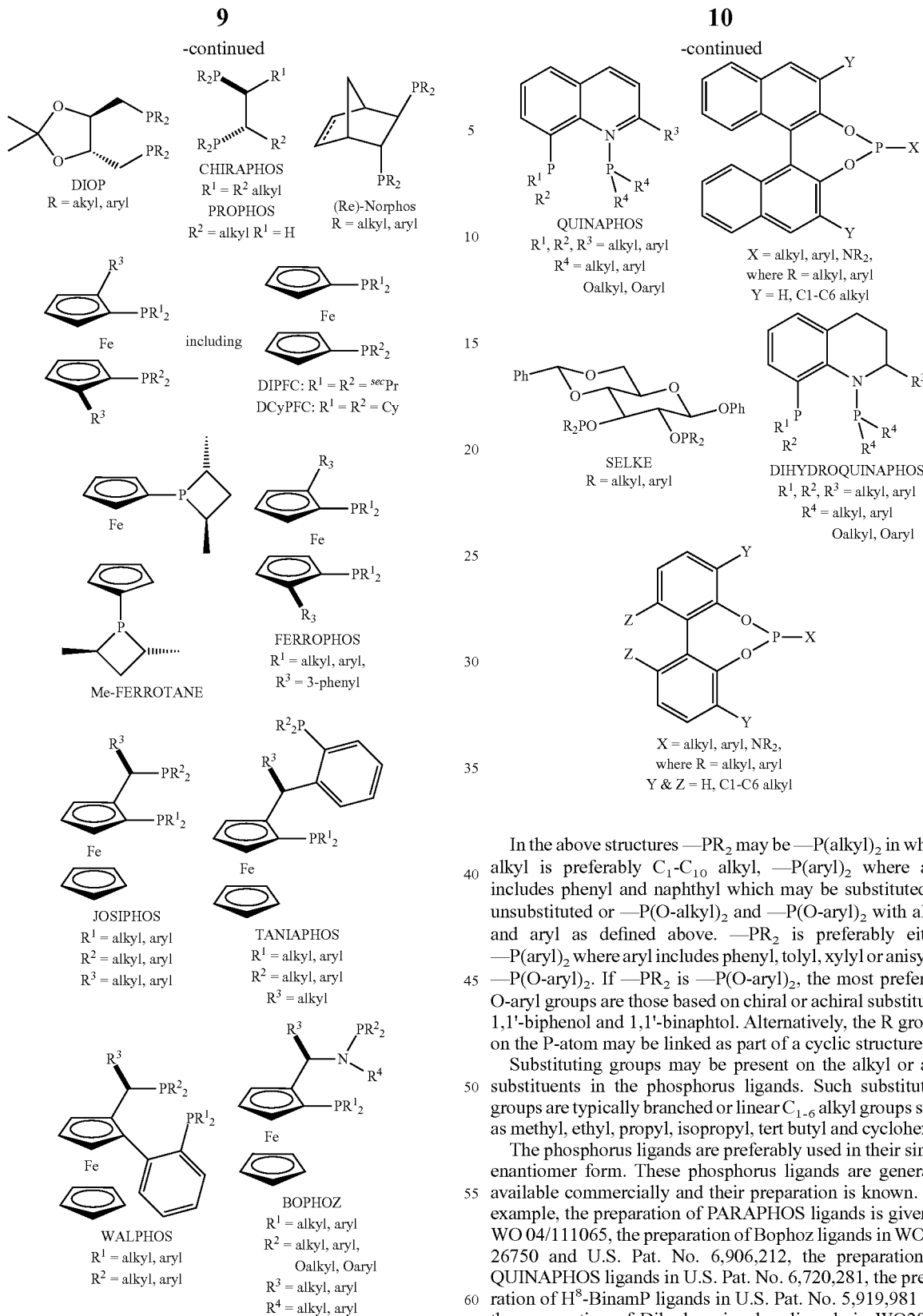

In the above structures —PR$_2$ may be —P(alkyl)$_2$ in which alkyl is preferably C$_1$-C$_{10}$ alkyl, —P(aryl)$_2$ where aryl includes phenyl and naphthyl which may be substituted or unsubstituted or —P(O-alkyl)$_2$ and —P(O-aryl)$_2$ with alkyl and aryl as defined above. —PR$_2$ is preferably either —P(aryl)$_2$ where aryl includes phenyl, tolyl, xylyl or anisyl or —P(O-aryl)$_2$. If —PR$_2$ is —P(O-aryl)$_2$, the most preferred O-aryl groups are those based on chiral or achiral substituted 1,1'-biphenol and 1,1'-binaphtol. Alternatively, the R groups on the P-atom may be linked as part of a cyclic structure.

Substituting groups may be present on the alkyl or aryl substituents in the phosphorus ligands. Such substituting groups are typically branched or linear C$_{1-6}$ alkyl groups such as methyl, ethyl, propyl, isopropyl, tert butyl and cyclohexyl.

The phosphorus ligands are preferably used in their single enantiomer form. These phosphorus ligands are generally available commercially and their preparation is known. For example, the preparation of PARAPHOS ligands is given in WO 04/111065, the preparation of Bophoz ligands in WO02/26750 and U.S. Pat. No. 6,906,212, the preparation of QUINAPHOS ligands in U.S. Pat. No. 6,720,281, the preparation of H$^8$-BinamP ligands in U.S. Pat. No. 5,919,981 and the preparation of Dihydroquinaphos ligands in WO2008/041029.

Preferred phosphorus ligands include phenyl-di-t-butylphosphine, 1,2,3,4,5-pentaphenyl-1'-(di-t-butylphosphino)ferrocene, triphenylphosphine, tricyclohexylphosphine, tri(tert-butyl)phosphine, tris(p-tolyl)phosphine, tris(o-tolyl)phosphine, tris(p-methoxyphenyl)phosphine, di-tertbutyl-neopentylphosphine, tris(p-trifluoromethylphenyl) phosphine, tris(2,4,6-trimethoxyphenyl)phosphine, tris(2,4,6,-trimethyl)phosphine, tris(2,6-dimethylphenyl)phosphine, 1-adamantyl-di-t-butylphosphine, benzyldi-1-adamantylphosphine, butyldi-1-adamantylphosphine, cyclohexyldi-t-butylphosphine, cyclohexyldiphenylphosphine, 2-di-t-butylphosphino-1,1'-binaphtyl, 2-(di-t-butylphosphino) biphenyl, 2-di-t-butylphosphino-2'-(N,N-dimethylamino) biphenyl, 2-di-t-butylphosphino-2'-methylbiphenyl, 2-di-t-butylphosphino-2',4',6'-tri-i-propyl-1,1'-biphenyl, 2-di-t-butylphosphino-3,4,5,6-tetramethyl-2',4',6'-tri-l-propylbiphenyl, 2-(dicyclohexylphosphino) biphenyl, 2-(dicyclohexylphosphino)-2',6'-dimethoxy-1,1'-biphenyl, 2-di-t-cyclohexyl phosphino-2'-(N,N-dimethylamino)biphenyl, 2-di-t-cyclohexylphosphino-2',6'-di-i-propoxy-1,1'-biphenyl, 2-(dicyclohexylphosphino)-2',4',6'-tri-l-propyl-1,1'-biphenyl, 2-di-cyclohexyl phosphino-2'-methylbiphenyl, 2-diphenylphosphino-2'-(N,N-dimethylamino)biphenyl, (4-dimethyl-aminophenyl)(tert-butyl)$_2$phosphine, 1,2-bis(di-tertbutylphosphinomethyl) benzene, 1,3-bis(di-tertbutylphosphinomethyl)propane, 1,2-bis(di-phenylphosphino methyl)benzene, 1,2-bis(di-phenylphosphino)ethane, 1,2-bis (diphenylphosphino) propane, 1,2-bis(di-phenyl phosphino) butane, 1,1'-bis(di-penylphosphino)ferrocene N-(2-methoxyphenyl)-2-(di-t-butylphosphino)pyrrole, 1-(2-methoxyphenyl)-2-(di-cyclohexylphosphino)pyrrole, N-phenyl-2-(di-t-butylphosphino)indol, N-phenyl-2-(di-t-butylphosphino)pyrrole, N-phenyl-2-(dicyclohexylphosphino)indol, N-phenyl-2-(di-cyclohexylphosphino)pyrrole or 1-(2,4,6-trimethylphenyl)-2(dicyclohexylphosphino) imidazole. Triphenylphosphine, tributylphosphine, 1,2,3,4,5-pentaphenyl-1'-(di-t-butylphosphino)ferrocene, tricyclohexylphosphine, tris(o-tolyl)phosphine, di-tert-butyl-neopentyl phosphine, phenyl-di-t-butylphosphine or (4-dimethyl-aminophenyl)(tert-butyl)$_2$phosphine are particularly preferred.

The ligand may be present in stoichiometric or excess to the Pd(II) complex, preferably in stoichiometric quantities. When stoichiometric quantities are utilised, the methodology does not require the use of excess expensive ligands (such as phosphines) as sacrificing reducing agents and thereby makes the whole process highly efficient and atom-economical for commercial production.

The ligand L may be added to the reaction mixture as a solution in at least one solvent. Suitable solvents will generally be similar to those previously mentioned in connection with the Pd(II) complex. Alcohols, aromatic solvents and/or ketones are preferred, especially methanol, ethanol, toluene and acetone.

The solvents which may be used in steps a and b may be the same or different. In one embodiment, the solvents may be single protic solvent (such as methanol or water) or a combination of protic solvents (e.g. water, ethanol and/or methanol). Alternatively, the solvents may be a combination of aprotic and protic solvents (such as toluene, acetone, methanol, ethanol and/or water).

If desired, step a and/or step b may be carried out under an inert atmosphere, such as under nitrogen or argon. Preferably, the ligand L is reacted under an inert atmosphere.

The reactants may be added in any suitable order, but in one preferred process of the invention, the ligand L together with a solvent (if used) is added to a reaction mixture of the Pd(II) complex in at least one solvent and the base in a solvent (if used). This order of steps desirably prepares Pd(0)L$_2$ complexes. In another preferred process of the invention, the base together with a solvent (if used) is added to a reaction mixture of the Pd(II) complex in at least one solvent and the ligand L in a solvent (if used). This order of steps desirably prepares Pd(0)L$_2$ or Pd(0)L$_4$ complexes.

In one embodiment, the Pd(0)1$_n$ complex prepared is selected from the group consisting of:
a. [t-Bu$_2$PhP]$_2$Pd;
b. [t-Bu$_2$(p-PhMe$_2$N)P]$_2$Pd;
c. [Cy$_3$P]$_2$Pd;
d. [t-Bu$_3$P]$_2$Pd;
e. [P(C$_5$H$_4$FeC$_5$Ph$_5$)(t-Bu)$_2$]$_2$Pd;
f. [(o-tol)$_3$P]$_2$Pd;
g. [t-Bu$_2$(neopentyl)P]$_2$Pd; and
h. Pd[PPh$_3$]$_4$.

In another aspect, the present invention provides a Pd(0)L$_2$ complex which is Pd[(4-dimethyl-aminophenyl)(tert-butyl)$_2$phosphine]$_2$.

The present invention also includes a Pd(0)L$_2$ complex which is Pd[di-tert-butyl-neopentylphosphine]$_2$, preferably obtainable according to the process as described above.

The process of the invention may be preferably carried out at one or more temperatures in the range of about −10° C. to about 120° C., more preferably about −5° C. to about 80° C. It is preferred that the temperature is maintained below the decomposition temperature, and so, when the Pd(II) complex, Pd(II) intermediates and/or the Pd(0)L$_n$ complexes are known to decompose within the temperature ranges given above, the temperature should be maintained below the decomposition temperature.

The reaction may be carried out for a period of from about several minutes to about 24 hours but is usually complete within about 10 hours. On completion, the Pd(0)L$_n$ complex is separated from the reaction mixture by any appropriate method which is dependent upon the physical form of the product. When the Pd(0)L$_n$ complex is a solid, for example, the complex may be filtered from the supernatant, optionally washed and dried. Drying may be performed using known methods, for example at temperatures in the range 10-60° C. and preferably 20-40° C. under 1-30 mbar vacuum for 1 hour to 5 days. If desired the complex may be recrystallised.

In yet another aspect, the invention provides Pd(II) complexes of formulae 2a or 2b and a process for the preparation thereof.

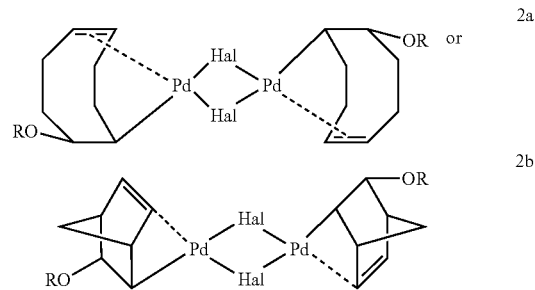

The process comprises the step of reacting Pd(diolefin)(Hal)$_2$ with (i) hydroxide in water, (ii) an alkoxide in solvent, or (iii) hydroxide in an alcohol ROH, optionally in at least one solvent,
wherein,
each Hal is independently a halide;
each R is independently H or an optionally substituted C$_{1-15}$ straight-chain, branched or cyclic alkyl group; and
the diolefin is cyclooctadiene or norbornadiene.

Suitable solvents and bases, as well as reaction and isolation conditions will generally be similar to those mentioned above.

In one preferred embodiment, the process comprises the step of reacting Pd(diolefin)(Hal)$_2$ with hydroxide in an alcohol ROH, optionally in at least one solvent. Preferably, the at least one solvent is at least one aprotic solvent, more preferably at least one aromatic and/or ethereal solvent and even more preferably, toluene and/or THF.

In still another aspect, the present invention provides a process for the preparation of a L$_2$Pd(H)(Hal) complex comprising the steps of:

a'. optionally preparing a Pd(II) complex of formula 2a or 2b:

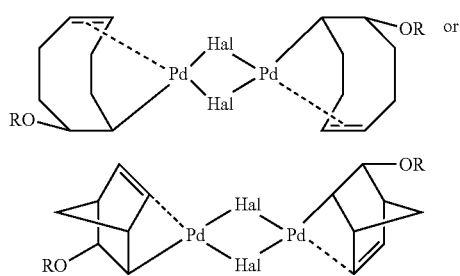

comprising reacting Pd(diolefin)(Hal)$_2$ with (i) hydroxide in water, (ii) an alkoxide in solvent, or (iii) hydroxide in an alcohol ROH, optionally in at least one solvent, wherein, each Hal is independently a halide;

each R is independently H or an optionally substituted C$_{1-15}$ straight-chain, branched or cyclic alkyl group; and the diolefin is cyclooctadiene or norbornadiene; and b'. reacting the Pd(ll) complex of formula 2a or 2b with ligand L and, if required, at least one solvent, to form the L$_2$Pd(H)(Hal) complex;

wherein, the at least one solvents of steps a' and b' are independently the same or different.

Suitable bases, solvents, ligands, as well as reaction and isolation conditions will be generally similar to those previously mentioned above.

The process is advantageous as the inventors are not aware of any efficient synthetically viable methods to access L$_2$Pd(H)(Hal) type of complexes.

In one embodiment, the process further comprises the step of:

c'. forming a Pd(0)L$_n$ complex wherein n is 2, 3 or 4;

When step a' is not carried out or the Pd(II) complex of formula 2a or 2b is isolated prior to carrying out step b', step c' may require the addition of further base in order to form the Pd(0)L$_n$ complex. However, when step a' is performed and the complex of formula 2a or 2b is prepared in situ, no further base may be necessary as there may be sufficient base remaining from step a'.

The complexes obtained by the methods of the present invention are pure and may contain very low or no by-products. In some embodiments, the complexes of the present invention have a purity ≥80%, in some embodiments ≥85%, in some embodiments ≥90%, in some embodiments ≥95%, in some embodiments ≥98%, in some embodiments ≥99%, in some embodiments ≥99.9%.

The invention will be further described in the following non-limiting Examples.

EXAMPLES

All solvents and reagents were purchased from commercial sources (e.g: Alfa Asear) and used as received. All ligands or precious metal precursors were obtained from Johnson Matthey Catalysis & Chiral Technologies or Alfa Aesar. All reactions were performed under inert atmosphere with Schlenk-line in conjunction with a Vacuum Atmosphere glove box. $^1$H, $^{13}$C and $^{31}$P-NMR spectra were recorded on a Bruker-400 MHz spectrometer at ambient temperature in C$_6$D$_6$ (Alfa Aesar). Elemental Analyses of all the compounds were done at Robertson Microlit Laboratories Inc., 29 Samson Ave., Madison, N.J. -07940.

Single crystals of di-μ-bromo[(1,4,5-η)-8-methoxy-4-cycloocten-1-yl]dipalladium,9Br and (Cy$_3$P)$_2$Pd(H)Br were obtained by slow diffusion from methanol/toluene and the structures were determined by X-ray analysis at University of Delaware, using APEX Bruker-AXS CCD X-ray diffractometer equipped with a monocap collimator. The crystallographic data were deposited at the Cambridge Crystallographic Data Center with the deposition numbers, CCDC 752566 and CCDC 752565 respectively.

Example 1

Synthesis of Di-μ-bromo[(1,4,5-η)-8-methoxy-4-cycloocten-1-yl]dipalladium,9Br

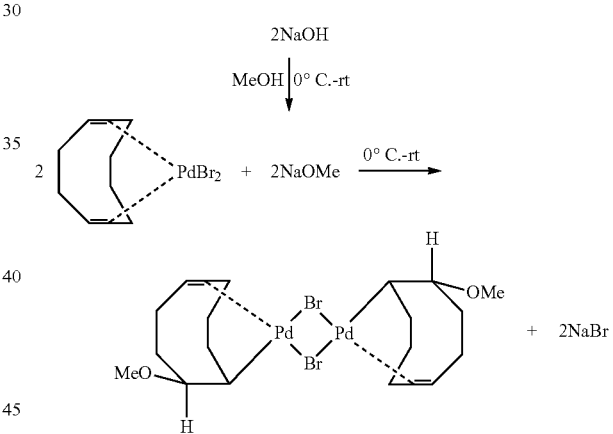

A solution of NaOH in 1 mL methanol (1.5 mmol, 0.06 g) was added to Pd(COD)Br$_2$ (1.3 mmol, 0.5 g) suspended in 2 mL toluene at 0° C. The resulting mixture was stirred for 15 minutes at 0° C. and filtered. The filtrate was evaporated under vacuum, washed with 1 mL cold methanol and dried under high vacuum to obtain the title product in 92% yield (off-white solid, 0.4 g). $^1$H NMR (C$_6$D$_6$,): δ (ppm) 5.83 (m, 2H), 5.64 (m, 2H), 4.11 (b,2H), 3.63 (m, 2H), 3.12(s, 6H), 1.40-2.20(m, 16H). $^{13}$C NMR (C$_6$D$_6$): δ (ppm) 107.9, 102.9, 81.6, 56.2, 53.4, 34.8, 31.1, 27.9, 26.5. Elemental analysis: C$_{18}$H$_{30}$Pd$_2$Br$_2$O$_2$; Calcd.: C, 33.21, H, 4.64; Found C, 33.08, H, 4.58.

The X-ray crystallographic structure of the title compound is given in FIG. 1. Thermal ellipsoids are shown at 50% probability (hydrogen atoms were omitted for clarity). Selected bond distances (Å) and angles (deg): C1-C2, 1.373 (9); C5-C6, 1.512(9); Pd—C6, 2.062(7); Pd—Br, 2.644(1); Br—Pd—Br, 88.55(2); C1-Pd—C6, 281.1(3).

The molecular structure of the organopalladium dimer reveals the oxypalladation of the COD via the nucleophilic attack of the MeO⁻ anion at one of its double bonds. The C1-C2 length of 1.373 Å is typical of a C═C double bond, while the C5-C6 distance (1.512 Å) indicates clearly a C—C single bond. The Pd—C6 distance is 2.062 Å, typical of a Pd—C σ bond.

Example 2

Synthesis of (Cy$_3$P)$_2$Pd(H)Br

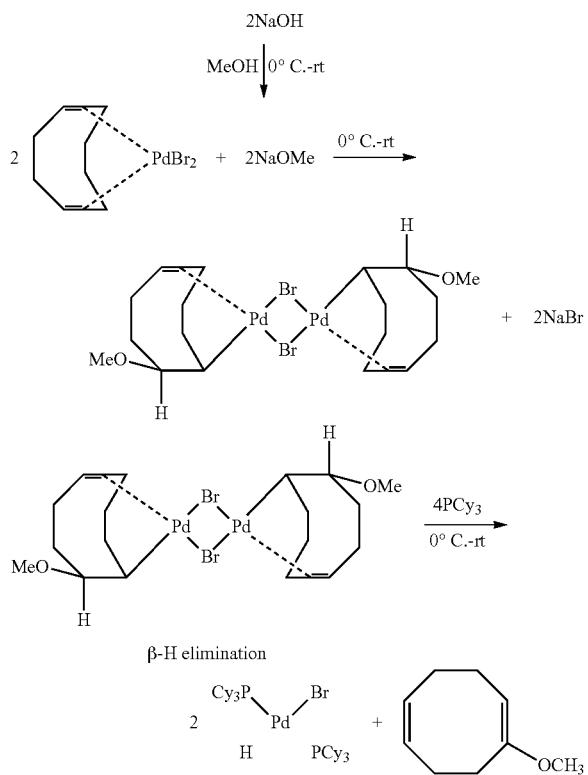

A solution of NaOH in methanol (2.7 mmol, 0.11 g, 1.5 mL MeOH) was added to Pd(COD)Br$_2$ (2.7 mmol, 1 g) suspended in 3.5 mL toluene at 0° C. The resulting solution was then reacted with tricyclohexylphosphine (Cy$_3$P) (5.4 mmol, 1.4 g) in 10 mL toluene under N$_2$ at 0° C. for 2 h. To this solution, 20 mL methanol was added to precipitate the product, which was subsequently filtered, washed with methanol (3×10 mL) and dried under high vacuum to obtain 1.7 g product as white solid in 85% yield. $^1$H NMR (C$_6$D$_6$): δ (ppm) 2.39 (t, 6H), 2.24 (d, 12H), 1.83 (m, 30H), 1.38 (m, 18H), −13.06 (1H). $^{31}$P NMR (C$_6$D$_6$): δ (ppm) 41.9 (s). Elemental analysis: C$_{36}$H$_{67}$BrP$_2$Pd; Calcd.: C, 57.79; H, 9.03; Br, 10.68; Found C, 57.83; H, 8.91; Br,10.32.

Figure 2:
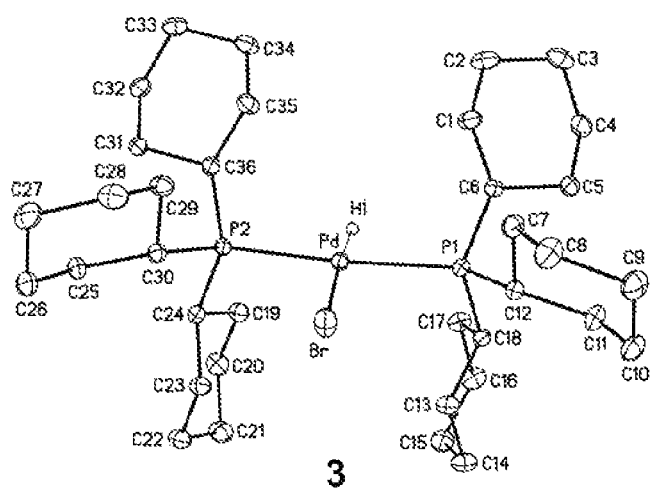
FIG. 2 is the X-ray crystallographic structure of $(Cy_3P)_2Pd(H)Br$.

The X-ray crystallographic structure of the title compound is given in FIG. 2. Thermal ellipsoids are shown at 50% probability (hydrogen atoms were omitted for clarity.) Selected bond distances (Å) and angles (deg): Pd—Br, 2.532 (1); Pd—P1, 2.308(1); P1-Pd—P2, 163.38(2); P1-Pd—Br, 98.43(5).

Example 3

Isolation of methoxy-cyclooctadiene

The filtrate from the above the procedure to synthesize (Cy$_3$P)$_2$Pd(H)Br was evaporated to dryness and the residue was extracted with 20 mL pentane. The solvent was evaporated and the product dried under high vacuum to afford the title product in 81% yield (yellow oil, 0.3 g).

This oil was found to be a mixture of two structural isomers: 1-methoxy-1,5-cyclooctadiene and 6-methoxy-1,4-cyclooctadiene with a ratio of 76:24 by NMR. $^1$H NMR (C$_6$D$_6$): 1-methoxy-1,5-cyclooctadiene δ (ppm) 5.69 (m, 2H), 4.60 (t, 1H), 3.35 (s, 3H), 1.2-2.6 (m, 8H). 6-methoxy-1,4-cyclooctadiene $^1$H NMR (C$_6$D$_6$): δ (ppm) 6.06 (b, 1H), 5.85 (b, 1H), 5.60-5.70 (m, 2H), 4.03 (m, 1H), 3.24(s, 3H), 1.2-2.37 (m, 6H). Elemental analysis: C$_9$H$_{14}$O; Calcd.: C, 78.21; H, 10.21. Found: C, 78.05, H, 10.09. GC-MS: m/z=138.3

Pd(0)L$_2$ Complexes

Example 4

Pd[P(t-Butyl)$_3$]$_2$

Pd(COD)Br$_2$ in toluene suspension was reacted with 2 mole equivalents of sodium hydroxide NaOH under −5° C. in methanol solution, the resulting solution was then reacted with 2 mole equivalents of tri(t-butyl)phosphine in toluene under N$_2$ at −5° C. for 0.5 h. More methanol was added and the reaction mixture was stirred for 1 hour to precipitate the product before filtered, washed with methanol to give product as bright white crystalline solid. Total yield=95%; NMR and elemental assay indicate pure product as Pd[P(t-Butyl)$_3$]$_2$. $^1$H NMR (C$_6$D$_6$): δ (ppm) 1.59 (t, 54H). $^{31}$P NMR (C$_6$D$_6$): δ 86.5 (s). Elemental analysis: C$_{24}$H$_{54}$P$_2$Pd; Calcd C, 56.40%; H, 10.65%; P, 12.12%; Found: C, 56.39%; H, 10.88%; P, 11.85%.

Example 5

Pd[t-Bu$_3$P]$_2$

Palladium cyclooctadiene dichloride Pd(COD)Cl$_2$ in water suspension was reacted with 4 mole equivalents of sodium hydroxide in water solution at room temperature for 10 min. The resulting slurry was then reacted with 2 mole equivalents of t-Bu$_3$P.HBF$_4$ at room temperature under N$_2$ for 3 h. The product was filtered, washed with water and dried to give product as an off-white solid. Total yield 85%. NMR indicated pure product as Pd[t-Bu$_3$P]$_2$ (Pd(0)).

Example 6

Pd[Q-Phos]$_2$(Q-Phos=1,2,3,4,5-pentaphenyl-1'-(di-t-butylphosphino)ferrocene)

Pd(COD)Br$_2$ in toluene suspension was reacted with 2 mole equivalents of sodium hydroxide NaOH under −5° C. in methanol solution, the resulting solution was then reacted with 2 mole equivalents of Q-Phos in toluene at −5° C. under N$_2$ for 2 h. Three more mole equivalents NaOH in methanol solution was added and the resulting reaction mixture was stirred at 50° C. for 6 h. More methanol was added to precipitate the product and the reaction mixture was stirred overnight at room temperature before filtered, washed with methanol to give product as bright pink solid. Total yield=95%. NMR and elemental assay indicate pure product as Pd[Q-Phos]$_2$ (Pd (0)). $^1$H NMR (THF-d$_8$): δ (ppm) 0.82 (d, 36H), 4.50 (br s, 4H), 4.75 (br s, 4H), 6.82-7.13 (m, 50H). $^{31}$P NMR (THF-d$_8$): δ (ppm) 59.0 (s). Elemental analysis: C$_{96}$H$_{94}$Fe$_2$P$_2$Pd; Calcd.: C, 75.47; H, 6.20; P, 4.05; Found: C, 74.96; H, 6.31;

P, 3.81. The analysis is consistent with the literature data (Mann, G.; Shelby, Q.; Roy, A. H.; Hartwig, J. F. *Organometallics*, 2003, 22, 2775).

Example 7

Pd[P(Cy$_3$)]$_2$

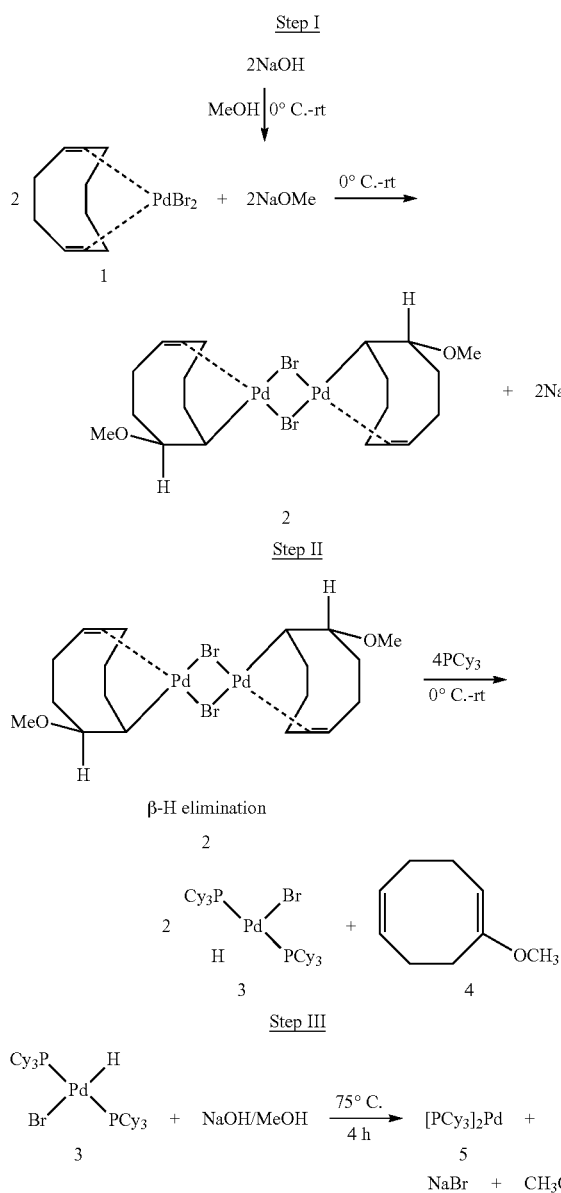

Pd(COD)Br$_2$ in toluene suspension was reacted with 4 mole equivalents of sodium hydroxide NaOH under −5° C. in methanol solution, the resulting solution was then reacted with 2 mole equivalents of tricyclohexylphosphine (PCy$_3$) in toluene under N$_2$ at −5° C. for 0.5 h and at room temperature for 0.5 h, then heated to 75° C. for 4 h. More methanol was added to precipitate the product before filtered, washed with methanol to give the product as an off white solid. Total yield=85%. NMR and elemental assay indicate pure product as Pd[P(Cy$_3$)]$_2$ (Pd(0)). $^1$H NMR (C$_6$D$_6$): δ (ppm) 2.34 (d, 12H), 1.95 (m, 18H), 1.80(m, 18H), 1.39 (m, 18H). $^{31}$P NMR (C$_6$D$_6$): δ (ppm) 39.2 (s) Elemental analysis: C$_{36}$H$_{66}$P$_2$Pd; Calcd.: C, 64.80; H, 9.97; P, 9.28; Found: C, 64.98; H, 9.83; P, 8.98.

Example 8

Pd[P(o-tol$_3$)]$_2$

Palladium cyclooctadiene dibromide Pd(COD)Br$_2$ in toluene suspension was reacted with 2 mole equivalents of sodium hydroxide NaOH under −5° C. in methanol solution, the resulting solution was then reacted with 2 mole equivalents of tris(ortho-tolyl)phosphine P(o-tol$_3$) in toluene at −5° C. under N$_2$ for 2 h. More methanol was added to precipitate the product and the reaction mixture was stirred overnight before filtered, washed with toluene and methanol to give product as bright yellow solid. Total yield=91%. Elemental assay indicated pure product as Pd[P(o-tol$_3$)]$_2$ (Pd(0)). $^1$H NMR (C$_6$D$_6$): δ (ppm) 7.20 (m, 18H), 6.91 (m, 6H), 3.09 (s, 18H), $^{31}$P NMR (C$_6$D$_6$): δ (ppm) −7.3 (s). Elemental analysis: C$_{42}$H$_{42}$P$_2$Pd; Calcd.: C, 70.54; H, 5.92; P, 8.66; Found: C, 70.41; H, 5.93; P, 8.59. The analysis is consistent with literature data (Paul, F.; Patt, J.; Hartwig, J. F. *Organometallics* 1995, 14, 3030).

Example 9

Pd[DtBNpP]$_2$
(DtBNpP=di-t-butyl-neopentylphosphine)

Palladium cyclooctadiene dibromide Pd(COD)Br$_2$ in methanol suspension was reacted with 2 mole equivalents of sodium hydroxide under −5° C. in methanol solution. The resulting slurry was then reacted with 2 mole equivalents of di-t-butyl-neopentylphosphine (DtBNpP) in methanol at −5° C. under N$_2$ for 2 h before filtered, washed with methanol to give product as an off-white solid. Total yield=85%. NMR and elemental assay indicate pure product as Pd[DtBNpP]$_2$ (Pd(0)). $^1$H NMR (C$_6$D$_6$): δ (ppm) 1.5 (s,br, 22H), 1.44 (t, 36H) $^{31}$P NMR (C$_6$D$_6$): δ 45.5 (s). Elemental analysis: C$_{26}$H$_{58}$P$_2$Pd; Calcd.: C, 57.93; H, 10.84; Found: C, 58.02; H, 10.80.

Example 10

Pd[(4-dimethyl-aminophenyl)(tert-butyl)$_2$phosphine]$_2$

Palladium cyclooctadiene dibromide Pd(COD)Br$_2$ in toluene suspension was reacted with 3 mole equivalents of sodium hydroxide NaOH under −5° C. in methanol solution, the resulting solution was then reacted with 2 mole equivalents [(4-dimethyl-aminophenyl)(tert-butyl)$_2$phosphine in toluene under N$_2$ at −5° C. for 0.5 h and at room temperature for 0.5 h, then heated to 60° C. for 0.5 h. More methanol was added to precipitate the product before filtered, washed with methanol to give product as off white solid. Total yield=85%. NMR and elemental assay indicate pure product as Pd[(4-dimethyl-aminophenyl)(t-butyl)$_2$P]$_2$ (Pd(0)). $^1$H NMR (C$_6$D$_6$): δ (ppm) 8.57 (b, 4H), 6.74 (d, 4H), 2.61(s, 12H), 1.76 (36H). $^{31}$P NMR (C$_6$D$_6$): δ 64.5 (s). Elemental analysis: C$_{32}$H$_{56}$P$_2$N$_2$Pd; Calcd.: C, 60.32; H, 8.86; P, 9.72; N, 4.40; Found: C, 60.04; H, 8.77; P, 9.60; N, 4.40.

Example 11

Pd[Ph(t-bu)$_2$P]$_2$

Palladium cyclooctadiene dibromide Pd(COD)Br$_2$ in methanol suspension was reacted with 3 mole equivalents of sodium hydroxide under −5° C. in methanol solution. The resulting slurry was then reacted with 2 mole equivalents of phenyl-di-t-butylphosphine Ph(t-Bu)$_2$P in methanol at −5° C. under N$_2$ for 4 h before filtered, washed with methanol to give product as an off-white solid. Total yield=95%. NMR and elemental assay indicate pure product as Pd[Ph(t-Bu)$_2$P ]$_2$ (Pd(0)). $^1$H NMR (C$_6$D$_6$): δ (ppm) 8.58 (b, 4H), 7.29 (m, 6H), 1.56 (t, 36H). 31$_{P\ NMR}$ (C$_6$D$_6$): δ (ppm) 67.6 ($_s$). Elemental analysis: C$_{28}$H$_{46}$P$_2$Pd; Calcd.: C, 61.03; H, 8.41; P, 11.24; Found: C, 60.58; H, 8.56; P, 10.95.

Pd(0)L$_4$ Complexes

Example 12

Pd[PPh$_3$]$_4$

Trans-dichloro-bis(triphenylphosphine)palladium dichloride, trans-(PPh$_3$)$_2$PdCl$_2$ in toluene suspension was reacted with 2 mole equivalents of triphenylphosphine (PPh$_3$) and 2 mole equivalents of sodium hydroxide in methanol solution at room temperature under N$_2$ for 2h. More methanol was added to precipitate the product before filtered, washed with methanol to give product as a bright yellow solid. Total yield 75%. NMR indicated pure product as Pd[PPh$_3$]$_4$ (Pd(0)).

Example 13

Pd[PPh$_3$]$_4$

Palladium cyclooctadiene dichloride Pd(COD)Cl$_2$ in methanol suspension was reacted with 2 mole equivalents of potassium hydroxide in methanol solution at room temperature for 0.5 h. The resulting slurry was then reacted with 2 mole equivalents of PPh$_3$ at room temperature under N$_2$ for 2 h. The product was filtered, washed with water and methanol to give product as a bright yellow solid. Total yield 93%. NMR and elemental assay indicated pure product as Pd[PPh$_3$]$_4$ (Pd(0)).

Example 14

Pd[PPh$_3$]$_4$

Palladium dichloride aqueous solution (0.21 kg Pd/1 kg solution) was mixed with ethanol and was reacted with 4 mole equivalents of PPh$_3$ in ethanol at room temperature for 0.5 h. The resulting slurry was reacted with 5.5 mole equivalents potassium hydroxide (25% w/w in H$_2$O) and the resulting yellow slurry was stirred at 70° C. under N$_2$ for 3 h, followed by cooling to room temperature, filtration, washing with 10% H$_2$O/ethanol, H$_2$O, and ethanol, and drying to give the product as a bright yellow solid. Total yield 82%. NMR indicated pure product as Pd[PPh$_3$]$_4$ (Pd(0)).

Example 15

Pd[PPh$_3$]$_4$

Palladium dichloride PdCl$_2$ was reacted with 2 mole equivalents of NH$_4$Cl in methanol at 60° C. for 1.5 h. The resulting slurry was reacted with 4 mole equivalents of PPh$_3$ in toluene at 60° C. for 10 min. The yellow slurry was reacted with 2 mole equivalents of [Bu$_4$N]OH solution (50% w/w in H$_2$O) at 60° C. under N$_2$ for 1 h, followed by cooling to room temperature, filtration, washing with methanol, H$_2$O, and methanol and drying to give the product as a bright yellow solid. Total yield 66%. NMR indicated pure product as Pd[PPh$_3$]$_4$ (Pd(0)).

Example 16

Pd[PPh$_3$]$_4$

Palladium dichloride aqueous solution (0.21 kg Pd/1 kg solution) was mixed with methanol and reacted with 4 mole equivalents of PPh$_3$ in toluene at 60° C. for 10 min. The yellow slurry was reacted with 5.5 mole equivalents [Bu$_4$N]OH solution (50% w/w in H$_2$O) at 60° C. under N$_2$ for 2 h, followed by more methanol addition to precipitate the product, cooling to room temperature, filtration, washing with methanol and drying to give the product as a bright yellow solid. Total yield 85%. NMR and elemental assay indicated pure product as Pd[PPh$_3$]$_4$ (Pd(0)).

Example 17

Pd[PPh$_3$]$_4$

Palladium dichloride PdCl$_2$ was reacted with 2 mole equivalents of KCl in methanol at 60° C. for 1.5 h. The resulting slurry was reacted with 4 mole equivalents of PPh$_3$ in toluene at 60° C. for 10 min. The yellow slurry was reacted with 2 mole equivalents of KOH solution in methanol at 60° C. under N$_2$ for 3 h, followed by methanol addition, cooling to room temperature, filtration, washing with 20% H$_2$O/methanol, and methanol and drying to give the product as a bright yellow solid. Total yield 89%. NMR indicated pure product as Pd[PPh$_3$]$_4$ (Pd(0)).

Example 18

Pd[PPh$_3$]$_4$

Palladium dichloride PdCl$_2$ was reacted with 2 mole equivalents of NaBr in EtOH at 60° C. for 1.5 h. The resulting slurry was reacted with 4 mole equivalents of PPh$_3$ in toluene at 60° C. for 1 h. The yellow slurry was reacted with 2 mole equivalents of KOH solution in methanol at 60° C. under N$_2$ for 3 h, followed by cooling to room temperature, addition of H$_2$O, filtration, washing with 30% H$_2$O/EtOH and EtOH, and drying to give the product as a bright yellow solid. Total yield 80%. NMR indicated pure product as Pd[PPh$_3$]$_4$ (Pd(0)).

Example 19

Pd[PPh$_3$]$_4$

Palladium dichloride aqueous solution (0.21 kg Pd/1 kg solution) was mixed with methanol and was reacted with 4 mole equivalents of PPh$_3$ in acetone at 60° C. for 1 h. The resulting slurry was reacted with 5.5 mole equivalents potassium hydroxide (25% w/w in H$_2$O) and the resulting yellow slurry was stirred at 60° C. under N$_2$ for 1 h, followed by cooling to room temperature, filtration, washing with 30% H$_2$O/methanol, H$_2$O, and methanol and drying to give the product as a bright yellow solid. Total yield 80%. NMR indicated pure product as Pd[PPh$_3$]$_4$ (Pd(0)).

The invention claimed is:

1. A process for the preparation of a Pd(0)L$_n$ complex, where L is a ligand and n is 2, comprising the steps of:
   a. reacting a Pd(II) complex in at least one solvent with a base and a ligand L; and
   b. if required, adding further base, optionally in at least one solvent, to form the Pd(0)L$_n$ complex;
   wherein the at least one solvents in steps a and b are independently the same or different; and
   wherein the Pd(II) complex is selected from the group consisting of Pd(olefin)$_x$(Hal)$_2$, Pd(Hal)$_2$ and M$_2$Pd(Hal)$_4$, in which each Hal is independently a halide, M is a cation, x is 1 or 2, and wherein when x=1 the olefin is a diolefin and when x=2 the olefin is a mono-olefin.

2. The process according to claim 1, wherein the Pd(II) complex is Pd(olefin)$_x$(Hal)$_2$.

3. The process according to claim 1, wherein in step a, ligand L is added to a reaction mixture of the Pd(II) complex in at least one solvent and the base.

4. The process according to claim 1, wherein in step a, the base is added to a reaction mixture of the Pd(II) complex in at least one solvent and the ligand L.

5. The process according to claim 1, wherein the base is a hydroxide, alkoxide, carbonate, phosphate or acetate.

6. The process according to claim 1, wherein the at least one solvents in steps a and b are independently selected from the group consisting of protic solvents, aprotic solvents and combinations thereof.

7. The process according to claim 1, wherein ligand L is a phosphorus ligand.

8. The process according to claim 7, wherein the phosphorus ligand is chiral or achiral, monodentate or bidentate phosphorus ligand in which each phosphorus atom is covalently bonded to either 3 carbon atoms or to z heteroatoms and 3-z carbon atoms, where z =1, 2 or 3.

9. The process according to claim 8, wherein the heteroatom is selected from the group consisting of N and O.

10. The process according to claim 1, wherein ligand L is a phosphine selected from the group consisting of phenyl-di-t-butylphosphine, di-tert-butyl-neopentylphosphine, 1,2,3,4,5-pentaphenyl-1'-(di-t-butylphosphino)ferrocene, triphenylphosphine, tricyclohexyl phosphine, tri(tert-butyl) phosphine, tris(p-tolyl)phosphine, tris(o-tolyl)phosphine, tris(p-methoxyphenyl)phosphine, tris(p-trifluoromethylphenyl) phosphine, tris(2,4,6-trimethoxyphenyl)phosphine, tris (2,4,6,-trimethyl)phosphine, tris(2,6-dimethylphenyl)phosphine, 1-adamantyl-di-t-butylphosphine, benzyldi-1-adamantylphosphine, butyldi-1-adamantylphosphine, cyclohexyldi-t-butylphosphine, cyclohexyldiphenylphosphine, 2-di-t-butylphosphino-1,1'-binaphthyl, 2-(di-t-butylphosphino)biphenyl, 2-di-t-butylphosphino-2'-(N,N-dimethylamino)biphenyl, 2-di-t-butylphosphino-2'-methylbiphenyl, 2-di-t-butylphosphino-2',4',6'-tri-i-propyl-1,1'-biphenyl, 2-di-t-butylphosphino-3,4,5,6-tetramethyl-2',4',6'-tri-i-propylbiphenyl, 2-(dicyclohexylphosphino) biphenyl, 2-(dicyclohexylphosphino)-2',6'-dimethoxy-1,1'-biphenyl, 2-di-t-cyclohexyl phosphino-2'-(N, N-dimethylamino)biphenyl, 2-di-t-cyclohexylphosphino-2',6'-di-i-propoxy-1,1'-biphenyl, 2-(dicyclohexylphosphino)-2',4',6'-tri-i-propyl-1,1'-biphenyl, 2-di-cyclohexyl phosphino-2'-methylbiphenyl, 2-diphenylphosphino-2'-(N,N-dimethylamino)biphenyl, (4-dimethyl-aminophenyl)(tert-butyl)$_2$phosphine, 1,2-bis(di-tertbutylphosphinomethyl)benzene, 1,3-bis(di-tertbutylphosphinomethyl)propane, 1,2-bis(di-phenylphosphino methyl)benzene, 1,2-bis(di-phenylphosphino)ethane, 1,2-bis(diphenylphosphino) propane, 1,2-bis(di-phenyl phosphino)butane, 1,1'-bis(di-phenylphosphino)ferrocene, N-(2-methoxyphenyl)-2-(di-t-butylphosphino)pyrrole, 1-(2-methoxyphenyl)-2-(di-cyclohexylphosphino)pyrrole, N-phenyl-2-(di-t-butylphosphino)indol, N-phenyl-2-(di-t-butylphosphino)pyrrole, N-phenyl-2-(di-cyclohexylphosphino)indol, N-phenyl-2-(di-cyclohexylphosphino)pyrrole and 1-(2,4,6-trimethylphenyl)-2(dicyclohexylphosphino)imidazole.

11. The process according to claim 1, wherein the Pd(0)L$_n$ complex is selected from the group consisting of:
   a. [t-Bu$_2$PhP]$_2$Pd;
   b. [t-Bu$_2$(p-PhMe$_2$N)P]$_2$Pd;
   c. [Cy$_3$P]$_2$Pd;
   d. [t-Bu$_3$P]$_2$Pd;
   e. [P(C$_5$H$_4$FeC$_5$Ph$_5$)(t-Bu)$_2$]$_2$Pd;
   f. [(o-tol)$_3$P]$_2$Pd; and
   g. [t-Bu$_2$(neopentyl)P]$_2$Pd.

12. A process for the preparation of a Pd(0)L$_n$ complex, where L is a ligand and n is 3 or 4, comprising the steps of:
   a. reacting a Pd(II) complex in at least one solvent with a base and a ligand L; and
   b. if required, adding further base, optionally in at least one solvent, to form the Pd(0)L$_n$ complex;
   wherein the at least one solvents in steps a and b are independently the same or different.

13. The process according to claim 12, wherein n is 4.

14. The process according to claim 12, wherein in step a, ligand L is added to a reaction mixture of the Pd(II) complex in at least one solvent and the base.

15. The process according to claim 12, wherein in step a, the base is added to a reaction mixture of the Pd(II) complex in at least one solvent and the ligand L.

16. The process according to claim 12, wherein the Pd(II) complex is selected from the group consisting of Pd(olefin)$_x$(Hal)$_2$, Pd(Hal)$_2$, Pd(phosphine)$_y$(Hal)$_2$ and M$_2$Pd(Hal)$_4$, in which each Hal is independently a halide, M is a cation, and x and y are independently 1 or 2, and wherein when x =1 the olefin is a diolefin, when x =2 the olefin is a mono-olefin, when y =1 the phosphine is a bidentate phosphine, and when y =2 the phosphine is a monophosphine.

17. The process according to claim 12, wherein the base is a hydroxide, alkoxide, carbonate, phosphate or acetate.

18. The process according to claim 12, wherein the at least one solvents in steps a and b are independently selected from the group consisting of protic solvents, aprotic solvents and combinations thereof.

19. The process according to claim 12, wherein ligand L is a phosphorus ligand.

20. The process according to claim 19, wherein the phosphorus ligand is chiral or achiral, monodentate or bidentate phosphorus ligand in which each phosphorus atom is covalently bonded to either 3 carbon atoms or to z heteroatoms and 3-z carbon atoms, where z =1, 2 or 3.

21. The process according to claim 20, wherein the heteroatom is selected from the group consisting of N and O.

22. The process according to claim 12, wherein ligand L is a phosphine selected from the group consisting of phenyl-di-t-butylphosphine, di-tert-butyl-neopentylphosphine, 1,2,3,4, 5-pentaphenyl-1'-(di-t-butylphosphino)ferrocene, triphenylphosphine, tricyclohexyl phosphine, tri(tert-butyl) phosphine, tris(p-tolyl)phosphine, tris(o-tolyl)phosphine, tris(p-methoxyphenyl)phosphine, tris(p-trifluoromethylphenyl) phosphine, tris(2,4,6-trimethoxyphenyl)phosphine, tris (2,4,6,-trimethyl)phosphine, tris(2,6-dimethylphenyl)phosphine, 1-adamantyl-di-t-butylphosphine, benzyldi-1-adamantylphosphine, butyldi-1-adamantylphosphine, cyclohexyldi-t-butylphosphine, cyclohexyldiphenylphosphine, 2-di-t-butylphosphino-1,1'-binaphthyl, 2-(di-t-butylphosphino)biphenyl, 2-di-t-butylphosphino-2'-(N,N-dimethylamino)biphenyl, 2-di-t-butylphosphino-2'-methylbiphenyl, 2-di-t-butylphosphino-2',4',6'-tri-i-propyl-1,1'-biphenyl, 2-di-t-butylphosphino-3,4,5,6-tetramethyl-2',4',6'-tri-i-propylbiphenyl, 2-(dicyclohexylphosphino) biphenyl, 2-(dicyclohexylphosphino)-2',6'-dimethoxy-1,1'-biphenyl, 2-di-t-cyclohexyl phosphino-2'-(N, N-dimethylamino)biphenyl, 2-di-t-cyclohexylphosphino-2',6'-di-i-propoxy-1,1'-biphenyl, 2-(dicyclohexylphosphino)-2',4',6'-tri-i-propyl-1,1'-biphenyl, 2-di-cyclohexyl phosphino-2'-methylbiphenyl, 2-diphenylphosphino-2'-(N, N-dimethylamino)biphenyl, (4-dimethyl-aminophenyl)(tert-butyl)$_2$phosphine, 1,2-bis(di-tertbutylphosphinomethyl)benzene, 1,3-bis(di-tertbutylphosphinomethyl)propane, 1,2-bis(di-phenylphosphino methyl)benzene, 1,2-bis(di-phenylphosphino)ethane, 1,2-bis(diphenylphosphino) propane, 1,2-bis(di-phenyl phosphino)butane, 1,1'-bis(di-phenylphosphino)ferrocene, N-(2-methoxyphenyl)-2-(di-t-butylphosphino)pyrrole, 1-(2-methoxyphenyl)-2-(di-cyclohexylphosphino)pyrrole, N-phenyl-2-(di-t-butylphosphino)indol, N-phenyl-2-(di-t-butylphosphino)pyrrole, N-phenyl-2-(dicyclohexylphosphino)indol, N-phenyl-2-(di-cyclohexylphosphino)pyrrole and 1-(2,4,6-trimethylphenyl)-2-(dicyclohexylphosphino)imidazole.

23. The process according to claim 12, wherein the Pd(0)L$_n$ complex is Pd[PPh$_3$]$_4$.

24. A process for the preparation of a Pd(II) complex of formula 2a or 2b:

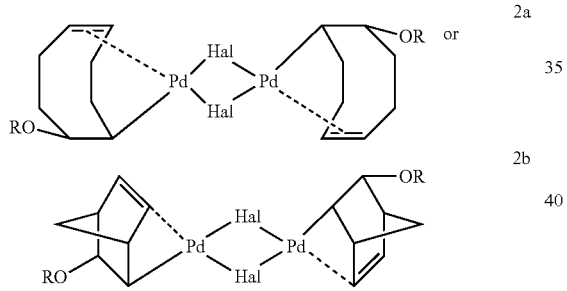

comprising reacting Pd(diolefin) (Hal)$_2$ with (i) hydroxide in water, (ii) an alkoxide in at least one solvent, or (iii) hydroxide in an alcohol ROH, optionally in at least one solvent, in which each Hal is independently a halide, each R is independently H or an optionally substituted C$_{1-15}$ straight-chain, branched or cyclic alkyl group and the diolefin is cyclooctadiene or norbornadiene.

25. A process for the preparation of a L$_2$Pd(H)(Hal) complex comprising the steps of:
    a'. optionally preparing a Pd(II) complex of formula 2a or 2b:

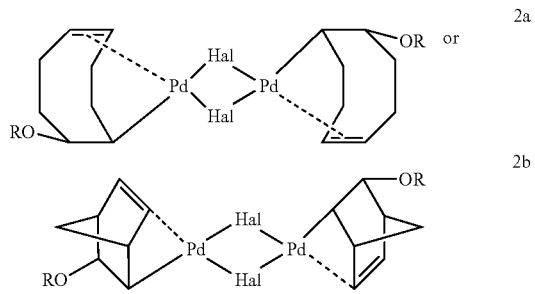

comprising reacting Pd(diolefin)(Hal)$_2$ with (i) hydroxide in water, (ii) an alkoxide in at least one solvent, or (iii) hydroxide in an alcohol ROH, optionally in at least one solvent, wherein each Hal is independently a halide, each R is independently H or an optionally substituted C$_{1-15}$ straight-chain, branched or cyclic alkyl group and the diolefin is cyclooctadiene or norbornadiene; and
    b'. reacting the Pd(II) complex of formula 2a or 2b with ligand L and, if required, at least one solvent, to form the L$_2$Pd(H)(Hal) complex;
    wherein the at least one solvents of steps a' and b' are independently the same or different.

26. The process according to claim 25, further comprising the step of:
    c'. forming a Pd(0)L$_n$ complex wherein n is 2, 3 or 4.

27. A Pd(II) complex of formula 2a:

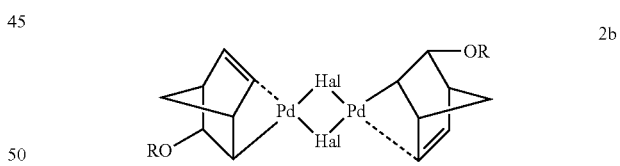

wherein each Hal is independently a halide, and each R is independently a substituted C$_{1-15}$ straight-chain alkyl group, or an optionally substituted C$_{1-15}$ branched or cyclic alkyl group.

28. A Pd(II) complex of formula 2b:

wherein each Hal is independently a halide, and each R is independently H or an optionally substituted C$_{1-15}$ straight-chain, branched or cyclic alkyl group.

29. A Pd(0)L$_2$ complex which is [t-Bu$_2$(p-PhMe$_2$N)P]$_2$Pd.

* * * * *